（12） United States Patent
Cheng et al.

US008652505B2

(10) Patent No.: US 8,652,505 B2
(45) Date of Patent: Feb. 18, 2014

(54) COATING FOR MEDICAL IMPLANTS

(75) Inventors: Xingguo Cheng, San Antonio, TX (US); Nitin Nitin, Vacaville, CA (US); Jorge G. Rossini, San Antonio, TX (US); Stephen T. Wellinghoff, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 330 days.

(21) Appl. No.: 12/717,666

(22) Filed: Mar. 4, 2010

(65) Prior Publication Data

US 2011/0217351 A1 Sep. 8, 2011

(51) Int. Cl.
*A61F 2/00* (2006.01)
*A61F 13/00* (2006.01)
*A61L 33/00* (2006.01)

(52) U.S. Cl.
USPC ........... 424/423; 424/422; 424/426; 427/2.24

(58) Field of Classification Search
USPC .................. 424/423, 422, 426; 427/2.24
See application file for complete search history.

(56) References Cited

U.S. PATENT DOCUMENTS

| 5,433,718 | A | 7/1995 | Brinker |
| 5,824,048 | A * | 10/1998 | Tuch ............................. 128/898 |
| 7,156,851 | B2 | 1/2007 | Christensen |
| 7,601,153 | B2 | 10/2009 | Shinjo et al. |
| 2004/0091605 | A1* | 5/2004 | Bayer et al. .................. 427/2.27 |
| 2005/0170071 | A1* | 8/2005 | Eramo ........................... 427/2.1 |
| 2005/0220837 | A1 | 10/2005 | Disegi et al. |
| 2007/0078513 | A1* | 4/2007 | Campbell .................... 623/1.44 |
| 2008/0254125 | A1 | 10/2008 | Freier |
| 2008/0262630 | A1 | 10/2008 | Fulmer et al. |
| 2009/0181098 | A1 | 7/2009 | Garrett et al. |

FOREIGN PATENT DOCUMENTS

WO 2005089825 9/2005

OTHER PUBLICATIONS

Greg T. Hermanson, 5-Heterobifunctional Cross-linkers, Bioconjugate Techniques, Academic Press, San Diego, 1996, pp. 228-286, ISBN 9780123423351, 10.1016/B978-012342335-1/50006-3. (http://www.sciencedirect.com/science/article/pii/B9780123423351500063).*
Adams, et al., "Controlled Release of Vancomycin from Thin Sol-Gel Films on Implant Surfaces Successfully Controls Osteomyelitis," Journal of orthopaedic research, 2009, vol. 27, No. 6, pp. 701-709.
Dejonge et al., "Organic-Inorganix Surface Modifications for Titanium Implant Surfaces," Pharm Res. Oct. 2008; 25(10):2357-69.
Monjo et al, "In vivo performance of absorbable collagen sponges with rosuvastatin," Acta Biomaterialia vol. 6, Issue 4, Apr. 2010, pp. 1405-1412.
Bajpai et al., "Enhanced water sorption of a semi-interpenetrating polymer network (IPN) of poly(2-hydroxyethyl methacrylate)(PHEMA) and poly(ethylene glycol)(PEG)," Journal of Macromolecular Science, Part A, vol. 39, Issue Jun. 7, 2002, pp. 667-692.
Zhang et al., "Synthesis and solubility of (mono-)end-functionalized poly(2-hydroxyethylmethacrylate-g-ethylene glycol) graft copolymers with varying macromolecular architectures," Macromolecules, 2005, 38 (6), pp. 2530-2534.
Casimiro, et al., "Drug release assays from new chitosan/pHEMA membranes obtained by gamma irradiation," Nuclear Instruments and Methods in Physics Research Section B: Beam Interactions with Materials and Atoms vol. 265, Issue 1, Dec. 2007, pp. 406-409.
Weaver, et al., "Stimulous-Responsive Water-Soluble Polymers Based on 2-Hydroxyethyl Methacrylate," Macromolecules 2004, 37, 2395-2403.
Meinig, "Clinical Use of Resorbable Polymeric Membranes in the Treatment of Bone Defects," Orthopedic Clinics of North America—vol. 41, Issue 1 (Jan. 2010) pp. 39-47.
Patel, et al., "Physicochemical Characterization and Dissolution Study of Solid Dispersions of Lovastatin with Polyethylene Glycol 4000 and Polyvinylpyrrolidone K30," Pharmaceutical Development and Technology, vol. 12, Issue 1 Jan. 2007, pp. 21-33.
Greene, et al., "Chitosan-coated Stainless Steel Screws for Fixation in Contaminated Fractures," Clinical Orthopaedics and Related Research vol. 466, No. 7; Jul. 2008, pp. 1699-1704.

* cited by examiner

*Primary Examiner* — Abigail Fisher
(74) *Attorney, Agent, or Firm* — Grossman, Tucker et al

(57) ABSTRACT

A medical implant for drug delivery comprising an inner layer of polymer material including a drug dispersed therein and an outer layer which may then mediate the release of the drug in a controllable manner. The outer layer may adhere and/or penetrate the underlying layer and offer a protective coating along with improved mechanical strength along with the ability to hydrate and become permeable to water and allow for drug release.

22 Claims, 10 Drawing Sheets

COATING FOR MEDICAL IMPLANTS

GOVERNMENT RIGHTS CLAUSE

This invention was made with United States Government support under Contract Award No. W8XWH-07-2-0119 awarded by the U.S. Army Medical Research Acquisition Activity. The Government has certain rights in this invention.

FIELD OF THE INVENTION

The present invention relates to coatings for medical implants. The implant may include an inner layer including a drug dispersed therein and an outer layer which may then mediate the release of the drug in a controllable manner. The outer polymeric layer may be configured to adhere or penetrate the underlying layer and therefore offer a protective coating to the underlying layer along with improved mechanical strength. The outer and inner layers may also be configured to partially and/or completely degrade in vivo and the coatings herein may find particular utility for intramedullary implants that may be inserted into bone cavities.

BACKGROUND

Controlled release of drugs from the area inside a bone (the medullar cavity) has been proposed for infection control and stimulation of bone growth during the repair of defects which do not normally heal. Intramedullary (IM) implants, which may be understood herein as implants for placement inside the bone have therefore been proposed, where such implants may include coatings to deliver appropriate drug therapy. However, problems persist when inserting such implants into a reamed IM canal, such as avoiding disruptions to the coating and thus altering the drug release profile in an uncontrollable fashion.

SUMMARY

In a first exemplary embodiment, the present invention relates to a method for coating the surface of an implant comprising:

(a) coating the implant surface with a first layer of polymeric material that is either physically adhered and/or covalently bound to the implant surface;

(b) coating the first layer of polymeric material with a second layer of polymeric material wherein the second layer of polymeric material includes a drug for delivery and wherein said second layer of polymeric material is either:
  (i) physically adhered to the first layer; and/or
  (ii) covalently bonded to the first layer; and/or
  (iii) joined to the first layer in the form of an interpenetrating polymer network; and (c) coating the second layer with a third outer layer wherein said third outer layer is either:
  (i) physically adhered to the second layer; and/or
  (ii) covalently bonded to the second layer; and/or
  (iii) joined to the second layer in the form of an interpenetrating polymer network;

wherein said third layer has relatively higher mechanical strength than said first and second layers and is capable of hydration and said implant provides an initial cumulative drug release within 24 hours of implantation of 0-95% and a sustained release of any remaining portion within a 14 day period.

In another exemplary embodiment, the present invention relates to a method for coating the surface of an implant comprising:

(a) coating the implant surface with a first layer of polymeric material that is either physically adhered and/or covalently bound to the implant surface wherein said first polymer material includes surface functionality comprising amine, hydroxyl and/or carboxylic acid groups;

(b) coating the first layer of polymeric material with a second layer of polymeric material wherein the second layer of polymeric material includes surface functionality comprising amine, hydroxyl and/or carboxylic acid and said second layer includes a drug for delivery and wherein said second layer of polymeric material is either:
  (i) physically adhered to the first layer; and/or
  (ii) covalently bonded to the first layer; and/or
  (iii) joined to the first layer in the form of an interpenetrating polymer network; and (c) coating the second layer with a third outer layer wherein said third outer layer is either:
  (i) physically adhered to the second layer; and/or
  (ii) covalently bonded to the second layer; and/or
  (iii) joined to the second layer in the form of an interpenetrating polymer network wherein said third outer layer comprises:

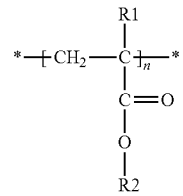

wherein R1 is selected from a hydrogen, alkyl group and/or an aromatic ring;

R2 is selected from: (1) an alkyl group wherein at least one hydrogen on the alkyl group may be substituted with a hydrophilic type functional group; (2) ether and/or polyether type functionality.

In a still further representative embodiment, the present disclosure relates to a method for coating the surface of an implant comprising:

(a) coating the implant surface with a first layer of polymeric material that is either physically adhered and/or covalently bound to the implant surface and which includes a drug for delivery;

(b) coating the first layer with a second outer layer wherein said second outer layer is either:
  (i) physically adhered to the first layer; and/or
  (ii) covalently bonded to the first layer; and/or
  (iii) joined to the first layer in the form of an interpenetrating polymer network;

wherein said outer layer has relatively higher mechanical strength than said first layer and is capable of hydration and said implant provides an initial cumulative drug release within 24 hours of implantation of 0-95% and a sustained release of any remaining portion within a 14 day period.

In yet another representative embodiment, the present disclosure relates to an implant comprising:

(a) an implant substrate including an outer surface wherein the implant is selected from one of: (i) a polymeric material; (ii) a ceramic material; or (iii) a metallic material selected from the group consisting of Ti, Al, V, Cr, Fe, Co, Mo, Ni, Mn, Mg, Zr, and combinations thereof and/or stainless steels;

(b) a first layer of polymeric material that is either physically adhered and/or covalently bound to the implant surface;

(c) a second layer of polymeric material wherein the second layer of polymeric material includes a drug for delivery and wherein said second layer of polymeric material is either:
  (i) physically adhered to the first layer; and/or
  (ii) covalently bonded to the first layer; and/or
  (iii) joined to the first layer in the form of an interpenetrating polymer network; and (d) a third outer layer wherein said third outer layer is either:
  (i) physically adhered to the second layer; and/or
  (ii) covalently bonded to the second layer; and/or
  (iii) joined to the second layer in the form of an interpenetrating polymer network;

wherein said third layer has relatively higher mechanical strength than said first and second layers and is capable of hydration and said implant provides an initial cumulative drug release within 24 hours of administration of 0-95% and a sustained release of any remaining portion within a 14 day period.

In another representative embodiment, the present disclosure relates to an implant comprising:

(a) an implant substrate including an outer surface wherein the implant is selected from one of: (i) a polymeric material; (ii) a ceramic material; or (iii) a metallic material selected from the group consisting of Ti, Al, V, Cr, Fe, Co, Mo, Ni, Mn, Mg, Zr, and combinations thereof and/or stainless steels;

(b) a first layer of polymeric material including a drug for delivery wherein said polymer material is either physically adhered and/or covalently bound to the implant surface wherein said first polymer material includes surface functionality comprising amine, hydroxyl and/or carboxylic acid groups;

(b) a second layer of polymeric material wherein said second layer is either:
  (i) physically adhered to the first layer; and/or
  (ii) covalently bonded to the first layer; and/or
  (iii) joined to the first layer in the form of an interpenetrating polymer network; and wherein said second layer comprises

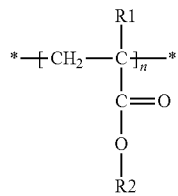

wherein R1 is selected from a hydrogen, alkyl group and/or an aromatic ring;

R2 is selected from: (1) an alkyl group wherein at least one hydrogen on the alkyl group may be substituted with a hydrophilic type functional group; (2) ether and/or polyether type functionality.

BRIEF DESCRIPTION OF THE DRAWINGS

The abovementioned and other features and advantages of the present invention, and the manner of attaining them, will become more apparent and the invention will be better understood by reference to the following description in conjunction with the accompanying drawings wherein.

DETAILED DESCRIPTION

The medical implants herein that are suitable for coating include any medical implant that may be positioned within a patient to provide release of a drug. The medical implant may therefore include an implant comprising a polymeric and/or ceramic type material, where reference to polymeric may be understood as any synthetic or natural polymeric material. Polymeric material may therefore include materials comprised of polymerizable monomer, monomers, dimers or trimers. They may comprise ethylenically unsaturated monomers or even an acrylate functional group. The term "monomers," as used herein, can also represent dimers, trimers, resins, resin components or any other polymerizable component. Reference to ceramic materials may be understood as inorganic, non-metallic materials that are prepared by the action of heat and cooling, and which are either crystalline, partially crystalline or amorphous. Preferably, the insert is a metallic material, and may be formed from one or metals selected from the group consisting of Ti, Al, V, Cr, Fe, Co, Mo, Ni, Mn, Mg, Zr, and combinations thereof such as Ti alloys, Mg alloys, and/or stainless steels (a steel alloy with a minimum of 10.5% chromium content by mass).

While the present disclosure is therefore preferably utilized in the context of an IM implant, prepared from the indicated metals, it is contemplated herein that the implant configuration herein may also be utilized as a dental, hip, knee, spine, ankle, finger, hand, and leg prostheses, cardiovascular prostheses, artificial devices related to lung, kidney, contact lens, intraocular devices, and as replacement for certain muscle and soft connective tissue.

Any one of the herein referenced implants may be selected and/or configured such that it offers a desired chemical surface functionality. More specifically, the surface of any of the above implants may be selected and/or configured such that it may include, e.g., acidic and/or basic type functionality to thereby promote either primary covalent bonding and/or secondary type polar type attractions (e.g. H-bonds or dipole-dipole association or van der Waals interactions) with respect to a selected coating layer treatment. For example, the surface of the implant may be configured to provide surface functionality (SF) including a hydroxyl (—OH) type group, carboxylic acid (—COOH) type group, and/or amine (—NH$_2$) type functionality. Preferably, one may therefore utilize chitosan, collagen, gelatin, chitin, cellulose material and or poly(ethylene glycol) (PEG).

Figure 1:
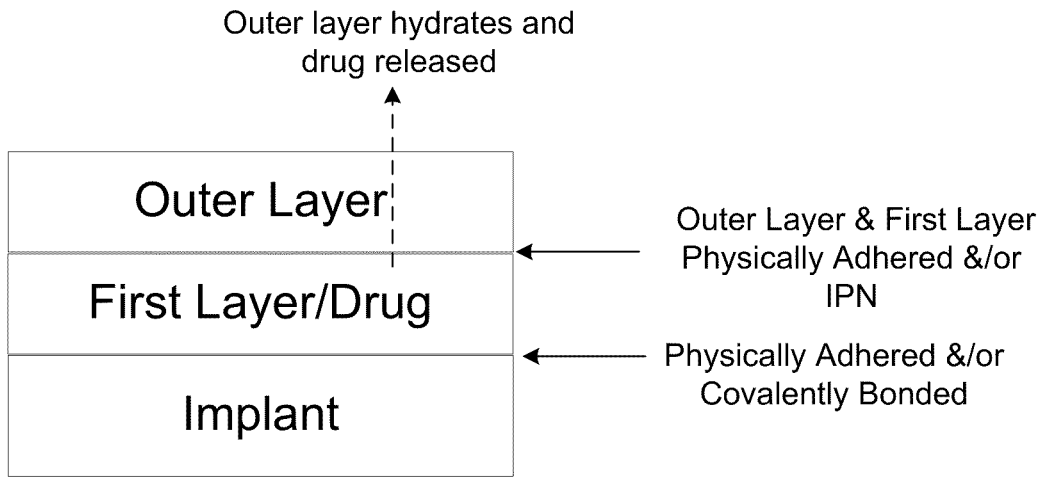
FIG. 1 is an illustration of one form of the implant herein.

On a general level, and as illustrated in FIG. 1, it may therefore be appreciated that for a selected implant, one may first deposit a coating layer on the implant where the first coating layer is either physically adhered on to the implant via secondary type polar attractions and/or bound to the implant via covalent bonds. This first layer may also include a selected drug dispersed therein for delivery. This first layer may have a thickness of 100 nanometers (nm) to 500 microns (μm). The first layer may provide a surface functionality such that amine (—NH$_2$) and/or hydroxyl (—OH) groups and/or carboxylic acid groups (—COOH) are available for covalent bonding and/or interpenetrating network formation, as disclosed herein.

This may then be followed by depositing a second layer which serves as the outer coating layer and which may be applied as a polymerizable monomer. Such polymerizable monomer may diffuse into the first layer and wherein subsequent polymerization will provide: (1) an interpenetrating polymer network (IPN) between the layers; and/or (2) physical adhesion between the layers which may be due to secondary type polar attraction. An IPN may be understood herein as comprising that situation wherein the polymers at issue (i.e. the polymers of the first and second layers) are interlaced on a polymer scale and which cannot be separated unless chemical bonds are broken. The outer coating layer may also have a thickness of 100 nm to 500 μm and may absorb 1.0% by weight to 50.0% by weight water.

The polymer of the outer coating layer is preferably selected such that it may modify the release characteristics of the underlying drug, in the sense that a desired release profile is obtained due to hydration (water absorbtion) of the outer coating layer. In addition, the outer coating layer is preferably selected such that it may also protect the underlying coating layers. For example, the outer coating layer is one that may now be inserted into a reamed IM canal such that the outer coating is preserved and the desired release profile is maintained. More specifically, as discussed in the examples which follow, the scratch resistance is improved and the drug release profile indicates, after an initial release, a sustained release for up to 14 days. For example, the release profile may comprise initial cumulative drug release within 24 hours of implantation of 0-95%, in 1% increments, and a sustained release of any remaining portion within a 14 day period, again in 1% increments. For example, one may then observe an initial burst release of 10% and then the cumulative release will increase to 100% within the 14 day period. Another example would lead to an initial burst release of 50% and then the cumulative release will again increase to 100% within a 14 day period. A still further example may indicate a burst release of 75% and a cumulative drug release within the remaining 14 day period of 25%. The ability to control the burst release and cumulative release in such fashion is therefore one very useful aspect of the medical implants herein which may therefore be further coordinated with respect to the location of the implant in the body as well as with respect to the type of drug that may be considered for delivery.

The outer coating layer may preferably be selected from a polymer that provides both hydrophobic and hydrophilic character. Accordingly, the corresponding monomer for the outer layer herein may have the following general structure:

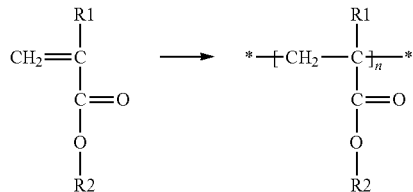

In the above, R1 may be selected from a hydrogen, alkyl group (e.g., —CH$_3$, —CH$_2$CH$_3$, —CH$_2$CH$_2$CH$_3$, etc.) and/or an aromatic ring, and R2 may be selected from an alkyl group (e.g. —CH$_3$, —CH$_2$CH$_3$, —CH$_2$CH$_2$CH$_3$) wherein at least one hydrogen on the alkyl group may be substituted with a hydrophilic type functional group such as a hydroxyl (—OH) type group and/or where R2 supplies an amide group (—NHCO—). R2 may also comprise ether type functionality (—OCH$_2$—) such that R2 may define an ethylene oxide type unit —OCH$_2$CH$_3$ or a poly(ethylene oxide) type structure —(OCH$_2$CH$_2$)$_n$—H where n has a value of 2-20. Accordingly, the outer coating layer may preferably be selected from polymers such as poly(2-hydroxylethyl methacrylate) (PHEMA) and/or poly(2-hydroxylpropyl methacrylate).

It is contemplated herein that the outer layer may also separately be formed of polcaprolactone, polylactic acid, and/or poly-lactic-co-glycolic acid type polymers. Such polymers may again be selected so that they similarly provide desirable release characteristics upon hydration and degradation in vivo as well as protection to the underlying implant prior to insertion to a desired location. It can be noted that in the case of poly-lactic-co-glycolic type resin, such polymer is relatively hydrophobic and will offer degradation in the body due to erosion and formation of microcracks, along with ensuing drug release, which microcrack formation may be accelerated by localized ester bond hydrolysis in either the polylactic or polyglycolic repeating units.

Figure 2:
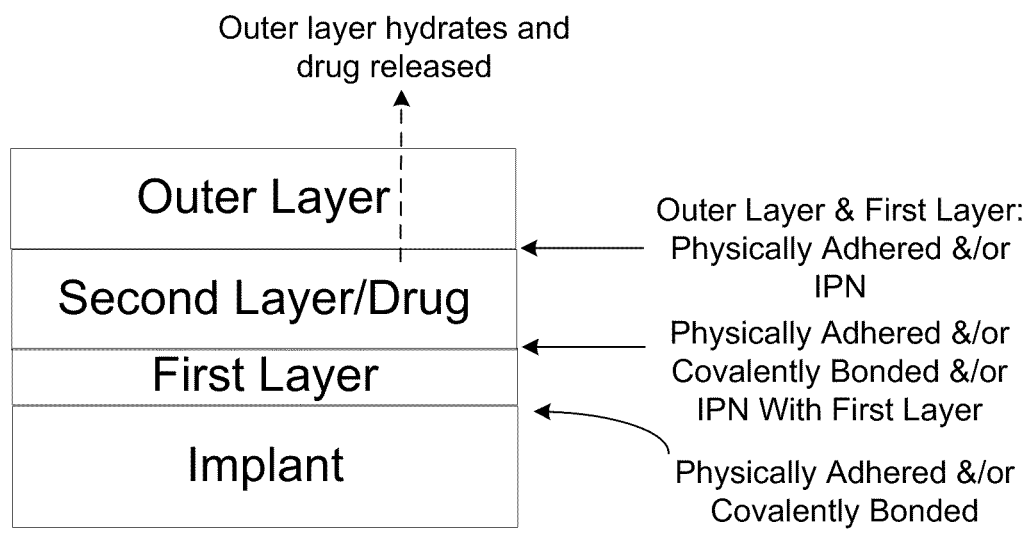
FIG. 2 is an illustration of one form of the implant herein.

With attention next directed to FIG. 2, for a selected implant, one may again first deposit a coating layer on the implant where the coating layer is either physically absorbed on to the implant via secondary type polar attractions and/or bound to the implant via covalent bonds. This first layer may have a thickness of 10 nanometers to 100 nanometer and may specifically serve to provide a more suitable layer and surface for adhering to the ensuing second polymer layer containing a dispersed drug. The first coating layer of FIG. 2 may therefore be the same polymer that was described above as the first coating layer in FIG. 1, but as noted, preferably present at a different thickness. Accordingly, it may contain surface functionality such that amine (—NH$_2$) and/or carboxylic acid (—COOH) and/or hydroxyl (—OH) groups are available for covalent bonding and/or interpenetrating network formation, as disclosed herein.

This may then be followed by deposition of a second layer at a thickness of 100 nm to 500 μm that may include a drug for release where the second layer may be applied as a monomer that may then be polymerized and which may then associate with the second layer by physically adhering (secondary type polar attractions), covalent bonding and/or IPN formation. Preferably, this second layer may have a thickness of 10 μm to 100 μm. Accordingly, the second layer may also be applied in polymeric form via melt coating or solvent evaporation (i.e. from a solution of polymer and drug). The second layer may also contain surface functionality such that amine (—NH$_2$)

and/or carboxylic acid (—COOH) and/or hydroxyl (—OH) groups may be available for covalent bonding and/or interpenetrating network formation, as disclosed herein. This may then be followed by application of a third outer coating layer, the characteristics of which were described above.

Figure 3:
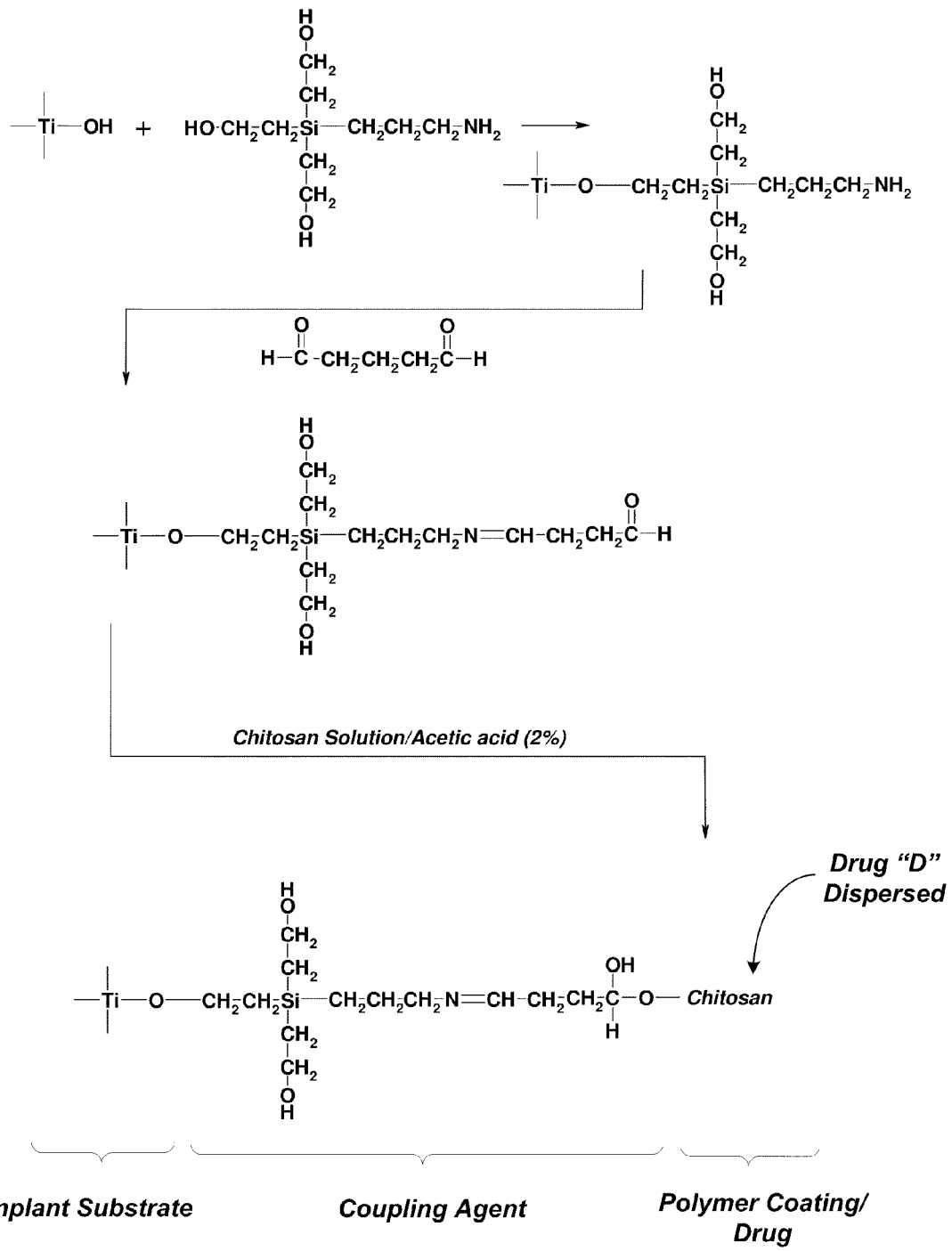
FIG. 3 illustrates the chemistry associated with the use of a coupling agent to form the implant herein.

One preferred procedure for modifying or enhancing the implant surface functionality, as illustrated in FIG. 3, includes first supplying a metallic based substrate, such as Ti, which may initially include surface hydroxyl type functionality. This surface may then be exposed to a coupling agent, which may be understood herein as a chemical compound that optimizes the bonding of the surface of the implant with a selected coating layer. A coupling agent may therefore include a silane coupling agent, which facilitates bonding to the surface of the metal via the hydroxyl functionality while providing requisite functionality to covalently attach to a first layer polymer material. For example, the metallic surface may be exposed to 3-amino-propyl-triethoxysilane (APTES) followed by treatment with glutaraldehyde solution and then reaction with a film-forming polymer (e.g. chitosan) to provide covalent bonding. For example, in the case of chitosan

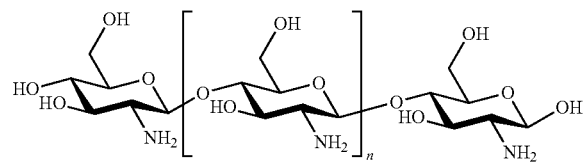

which itself contains pendant hydroxyl or amine functionality, either imine and/or hemiacetal type bonding may develop with surface hydroxyls associated with the metallic Ti substrate. In FIG. 3 chitosan is illustrated as developing a hemiacetal type covalent bond to the indicated silane coupling agent which would occur through via reaction of the hydroxyl groups on the chitosan with the aldehyde group, which may be facilitated in acidic conditions. However, as may be appreciated, the amine groups on the chitosan may react with the aldehyde group, as alluded to above, then providing covalent bonding via imine type linkages.

The film-forming polymer noted above (e.g. chitosan) may itself contain a drug dispersed therein for ensuing release. Such drug may simply be incorporated into the chitosan by dip coating in a solution containing a selected drug. In addition, as explained herein, this first layer of chitosan may be configured such that it does not contain any particular drug under those circumstances where a second polymer coating layer may include the drug of choice. See again, FIG. 2. The drugs that are therefore suitable for delivery within such protocol may be either hydrophilic (charge-polarized and capable of hydrogen bonding, enabling it to dissolve more readily in water than in oil) and/or hydrophobic (molecules that are non-polar and thus prefer other neutral molecules and nonpolar solvents). The drugs may be present in nanoparticle form, which may be understood as having a size of less than 1000 nm. The drugs herein may therefore be selected from any one or more of the following:

(1) Antibiotics. Exemplary antibiotics include tetracycline, aminoglycosides, penicillins, cephalosporins, sulfonamide drugs, chloramphenicol sodium succinate, erythromycin, vancomycin, lincomycin, clindamycin, nystatin, amphotericin B, amantidine, idoxuridine, p-amino salicyclic acid, isoniazid, rifampin, antinomycin D, mithramycin, daunomycin, adriamycin, bleomycin, vinblastine, vincristine, procarbazine, imidazole carboxamide, and the like.

(2) Anti-Tumor Agents. Exemplary anti-tumoral agents include proteosome inhibitors, doxorubicin, Daunorubicin, taxol, methotrexate, and the like. Exemplary antipyretics and analgesics include aspirin, Motrin, Ibuprofin, naprosyn, Indocin, acetaminophen, and the like.

(3) Anti-Inflammatory Agents. Exemplary anti-inflammatory agents include NSAIDS, aspirin, steroids, dexamethasone, hydrocortisone, prednisolone, Diclofenac Na, and the like.

(4) Therapeutic Agents. Exemplary therapeutic agents for treating osteoporosis and other factors acting on bone formation include Lovastatin, calcium, alendronate, bone GLa peptide, parathyroid hormone and its active fragments, histone H4-related bone formation and proliferation peptide and mutations, derivatives and analogs thereof.

(5) Enzymes and Enzyme Cofactors. Exemplary enzymes and enzyme cofactors include pancrease, L-asparaginase, hyaluronidase, chymotrypsin, trypsin, tPA, streptokinase, urokinase, pancreatin, collagenase, trypsinogen, chymotrypsinogen, plasminogen, streptokinase, adenyl cyclase, superoxide dismutase (SOD), and the like.

(6) Cytokines. Exemplary cytokines include transforming growth factors (TGFs), fibroblast growth factors (FGFs), platelet derived growth factors (PDGFs), epidermal growth factors (EGFs), connective tissue activated peptides (CTAPs), osteogenic factors, and biologically active analogs, fragments, and derivatives of such growth factors. Members of the transforming growth factor (TGF) supergene family, which are multifunctional regulatory proteins, are particularly preferred. Members of the TGF supergene family include the beta transforming growth factors (for example TGF-beta 1, TGF-beta 2, TGF-beta 3); bone morphogenetic proteins (for example, BMP-1, BMP-2, BMP-3, BMP-4, BMP-5, BMP-6, BMP-7, BMP-8, BMP-9); heparin-binding growth factors (for example, fibroblast growth factor (FGF), epidermal growth factor (EGF), platelet-derived growth factor (PDGF), insulin-like growth factor (IGF)); Inhibins (for example, Inhibin A, Inhibin B); growth differentiating factors (for example, GDF-1); and Activins (for example, Activin A, Activin B, Activin AB). Growth factors can be isolated from native or natural sources, such as from mammalian cells, or can be prepared synthetically, such as by recombinant DNA techniques or by various chemical processes. In addition, analogs, fragments, or derivatives of these factors can be used, provided that they exhibit at least some of the biological activity of the native molecule. For example, analogs can be prepared by expression of genes altered by site-specific mutagenesis or other genetic engineering techniques.

(7) Anticoagulants. Exemplary anticoagulants include warfarin, heparin, Hirudin, and the like.

(8) Immune System Factors. Exemplary factors acting on the immune system include factors which control inflammation and malignant neoplasms and factors which attack infective microorganisms, such as chemotactic peptides and bradykinins.

Figure 4:
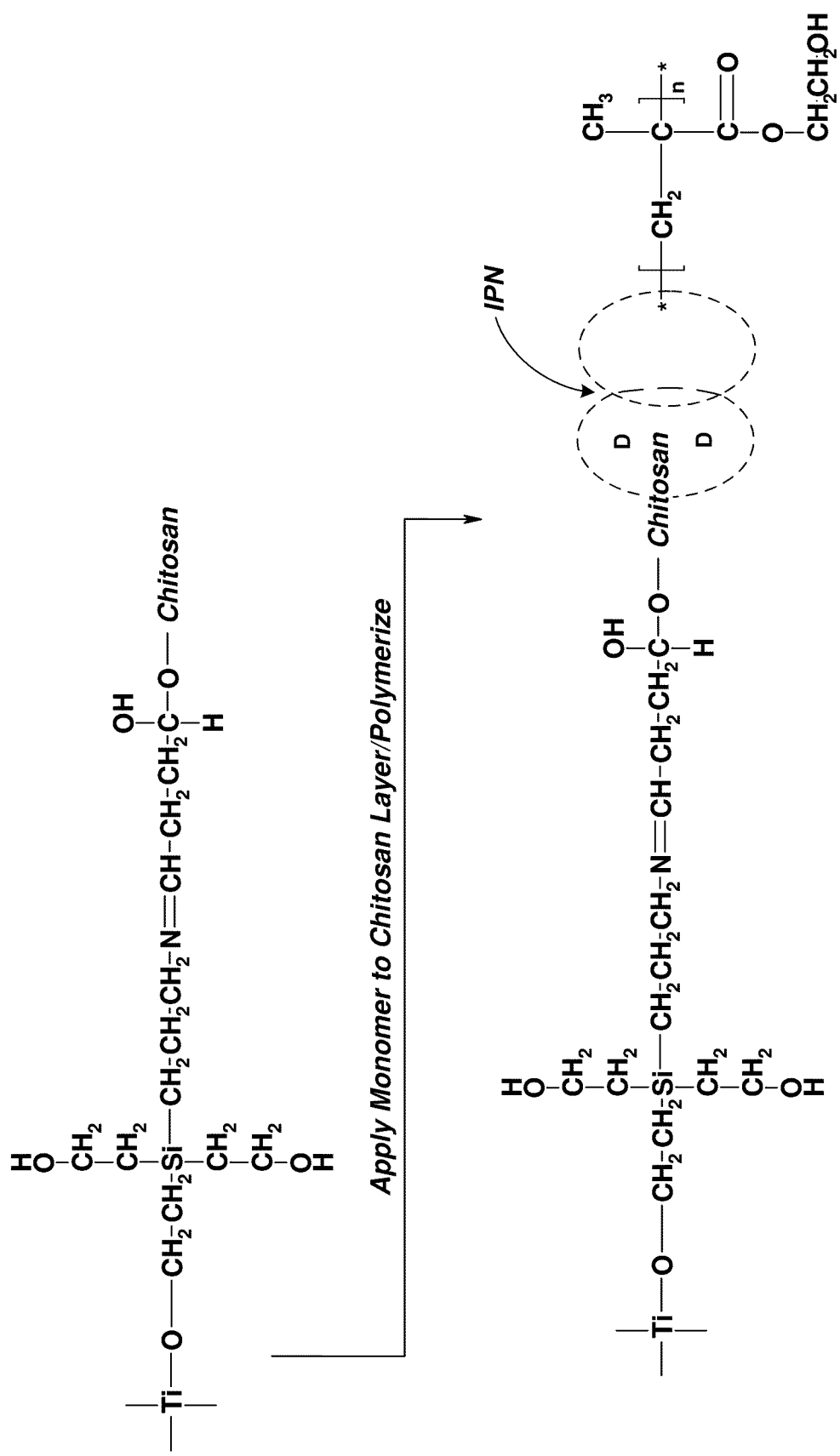
FIG. 4 further illustrates the chemistry associated with the forming of the implant coated surface herein.

Attention is next directed to FIG. 4, wherein the chitosan layer of FIG. 3 is exposed to a monomer, such as 2-hydroxyethylmethacrylate (HEMA). The monomer may then penetrate into the underlying layer depending upon the amount of time that the HEMA is allowed to diffuse into such layer prior to polymerization. The depth of penetration may therefore be on the order of 1.0 µm to 5.0 µm. Preferably, the depth of penetration may be 1-100 nm to provide acceptable diffusion and ensuing IPN formation. That is, as shown preferably, upon polymerization of the HEMA, an IPN is formed between the chitosan layer and the poly-HEMA. Upon hydration in vivo, the drug "D" may then be released.

As alluded to above, the present disclosure has particular utility with respect to IM nails that may now be coated with controlled release layers specifically containing hydrophilic antibiotics such as vancomycin and/or hydrophobic osteogenic agents such as lovastatin. Abrasion and cracking resistance of the coated IM nails is now improved and drug release modulated by overcoating the underlying layers with a photopolymerized (exposure to requisite light energy to induce polymerization) outer layer preferably based on polyhydroxyethylmethacrylate (PHEMA). This relatively hard overcoat permits insertion into the intermedullary cavity but later hydrates in body fluids enabling extended drug release from the underlying layers. Additionally random cracking and the consequent unpredictable drug release from the underlying layers is ameliorated. Further, the outer layer of PHEMA can be bound in an interpenetrating fashion to an underlying layer of polyethylene glycol (PEG) containing dispersed drug which has been shown to particularly aid in the release and improve the water solubility of the lipophilic lactone form of statin drugs. The PEG layer can in turn be coated onto the chitosan based layer, proximal to the oxidized Ti IM nail surface, as shown generally in FIG. 2 (where the implant would be a Ti IM nail, the first layer comprising chitosan and the second layer comprising PEG-lovastain and the outer layer comprising PHEMA).

It is therefore now useful to underscore the above and point out that many of the relatively more effective statins promoting bone growth are hydrophobic materials with relatively low water solubility (e.g. lovastatin, $T_m=165°$ C.). Therefore, to increase their effectiveness, their solubility in water may be enhanced with agents such as PEG (polyethylene glycol) which offers a relatively non-toxic, biocompatible material of low melting point (~55° C.) and is FDA approved for use in assisted drug delivery. Furthermore, 90% PEG and 10% lovastatin may form relatively stable solutions which will provide nanoemulsions of lovastatin in PEG. Higher concentrations may provide larger crystals of lovastatin in PEG. Accordingly, the use of PEG/lovastatin at concentrations of lovastatin in PEG of above 10% by weight, e.g. preferably in the range of 10% by weight to 50% by weight, now provides an opportunity for relatively efficient drug release into water or body fluids followed by relatively slow release from the relatively larger crystals of lovastatin which may occur via relatively slow dissolution of the hydrophobic lactone form or by hydrolysis of the lactone form into the ring opened, hydrophilic form. The ring opened form may then be delivered to the cell by active transport unlike the lipophilic form which diffuses across the cell membrane by passive transport. The ability to control the ratio of fast and slow drug release is important for optimizing bone growth at the correct stage and may now therefore be exploited in the present invention when the lovastatin at the above referenced concentrations within the PEG is utilized as one of the drug containing layers illustrated in FIG. 1 and/or FIG. 2.

IM nails can therefore be melt or solution coated with PEG-lovastatin to form the desired bone implants of the present invention. As noted, the PEG coating mechanical strength is observed to improve by overcoating with hydroxyethylmethacrylate (HEMA) and then photo or thermally polymerized to form a relatively harder outer coating of polyhydroxyethylmethacryate (PHEMA). As HEMA is partially soluble in PEG, HEMA monomer may penetrate into the interlamellar regions of the crystallized PEG and polymerization of this HEMA may generate a covalent bond layer between PEG-lovastatin and PHEMA layers which may comprise an interpenetrating network (IPN) of PHEMA and PEG. Covalent bonding between HEMA and PEG occurs when the PEG is methacrylate functionalized (e.g. as in 1,2-ethyleneglycol dimethacrylate or 1,4-butanediol dimethacrylate or poly(ethylene glycol) dimethacrylate where the ethylene glycol has a repeating unit value or "n" of 4-200). It should also be noted that upon formation of an IPN between PHEMA and PEG, the water swelling of the PHEMA can be observed to improve.

It is also worth noting that the lower critical solution temperature (LCST) of the PHEMA decreases with increasing degree of polymerization (number of repeating units or "n" in the indicated equations). The LCST may be understood as that the critical temperature below which the PHEMA is miscible in water in all proportions. PHEMA of DP of ≥45 exhibits a LCST of 37° C. at a pH of ≥6.5 where the PHEMA is water soluble below this temperature but insoluble above this temperature. The LCST for PHEMA is around body temperature at a DP of 34. Accordingly, when the PHEMA herein is utilized as an outer layer coating of the subject implants at DP values of higher than 34, and preferably at 40 or higher, the PHEMA will provide a swollen coating and modulate drug-release. Accordingly, it is preferably to utilize PHEMA in the range of greater than 34 and up to 100 to support primarily swelling of the PHEMA in the body environment. In addition, ultimately, the PHEMA coating may degrade away from the surface of the implant by breakup and dispersal of swollen PHEMA particles which may occur due to cell action. The advantage is that over time, the implant layers would then disappear into the body of a given patient.

More specifically, in the case of a PHEMA-PEG (lovastatin), upon exposure to water or body fluid the outer predominantly PHEMA layer will convert from a glassy to a relatively rubbery phase containing about 20-50% by weight water. As the water penetrates to the interpenetrating boundary region and into the PEG-lovastatin layer, PEG complexed lovastatin will now be released through the outer PHEMA layer into the surrounding body fluid. The remaining lovastatin crystals now exposed to the interpenetrating, water rich, PHEMA phase, will gradually dissolve over a much longer time frame consistent with maintaining the osteogenic potential of the statin.

In addition, the PHEMA may also include a selected amount of crosslinking. More specifically, the PHEMA monomer may include up to 10% by weight of a divinyl type monomer containing bioresorble crosslinks (e.g. crosslinking that may be hydrolyzed in the body environment). For example, one may utilize 1,2-ethyleneglycol dimethacrylate to provide a limited amount of crosslinking. In addition, it may be preferable to provide that the DP between crosslinks is ≤40 so that, as noted, the PHEMA may swell and degrade more efficiently into the body leaving behind, for example, a bone covered IM nail.

EXAMPLES

Example 1

Preparation of Vancomycin Coatings

Vancomycin-containing chitosan coating on Ti IM rods was produced where the chitosan first layer was covalently bound to the Ti rods to provide surfaces compatible with an applied vancomycin-chitosan second layer. The Ti rods were initially sonicated for 10 minutes each in 70% acetone, ethanol, and deionized water. The rods were then placed in nitric acid solution (3:7 v/v) for 30 min. at room temperature. The rods were then rinsed with water and placed in covered ultrapure water bath for 24 hrs. After incubation with 3-aminopropyl-triethoxy-silane solution for 24 hrs, the surface of the rods was then allowed to react with 2% glutaraldehyde solution for 24 hrs. The rods were removed and placed in a 1% chitosan solution in acetic acid (2%) for overnight. The rods were then washed with water and dried for later coating.

Vancomycin was then dissolved in 1% chitosan acetic acid-water solution at a concentration of (100 mg/mL) and 30 µl of the above solution was deposited onto the rods as they were rotated around their long axis at 1 RPM to produce the vancomycin second layer of about 27µ thickness by evaporation of the solvent. In order to stabilize the second layer against fracture and pealing and to control drug release, an outer layer of PHEMA was deposited on the second layer. Thus HEMA was mixed with a ca 1% (wt/wt) camphorquinone-amine photoinitiator to form a transparent homogenous monomer solution. 15 µl of this solution was deposited in yellow light on each vancomycin-chitosan coated Ti rod using the same coating procedure as used for the second coating and subsequently cured under blue light.

The surface morphology was then investigated utilizing scanning electron microscopy (Zeiss, EV)%) and scratch testing (CSM Instruments NanoScratch Tester, Serial No. 01-02526 with a spheroconical diamond indenter with a 20 µm radius and 90° angle, Serial No. SE-A16, mounted on a standard cantilever. The sample was held in place using a universal sample holder to ensure that the rod did not move during the analysis. More specifically, the diamond stylus is drawn across the surface of the coating at a constant speed and progressive normal force is applied. The force levels which produce a specific type/level of damage in the coating are defined as a critical scratch load.

Figure 5:
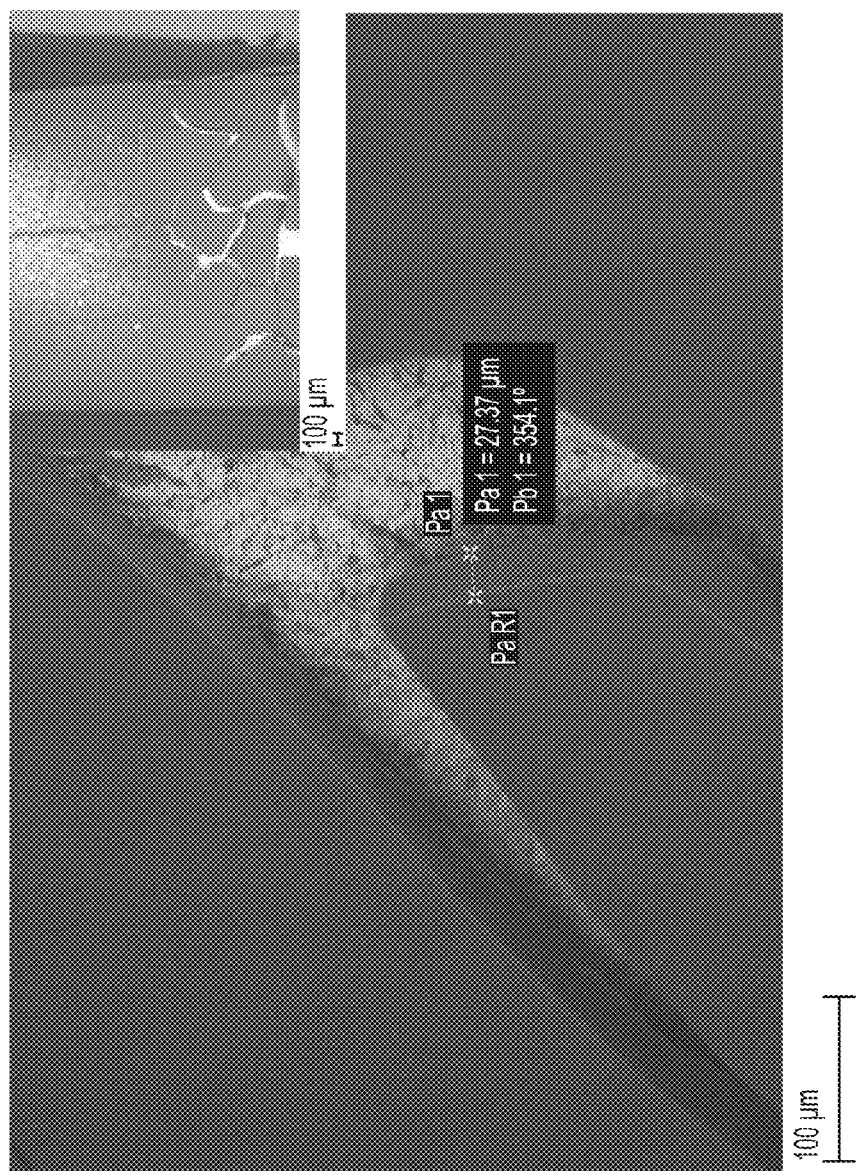
FIG. 5 is a scanning electron microscopy photograph of the surface of an implant containing a first covalently bound chitosan layer, a second chitosan layer including vancomycin dispersed therein in the absence of a PHEMA (poly(2-hydroxylethyl methacrylate)) layer.
Figure 6:
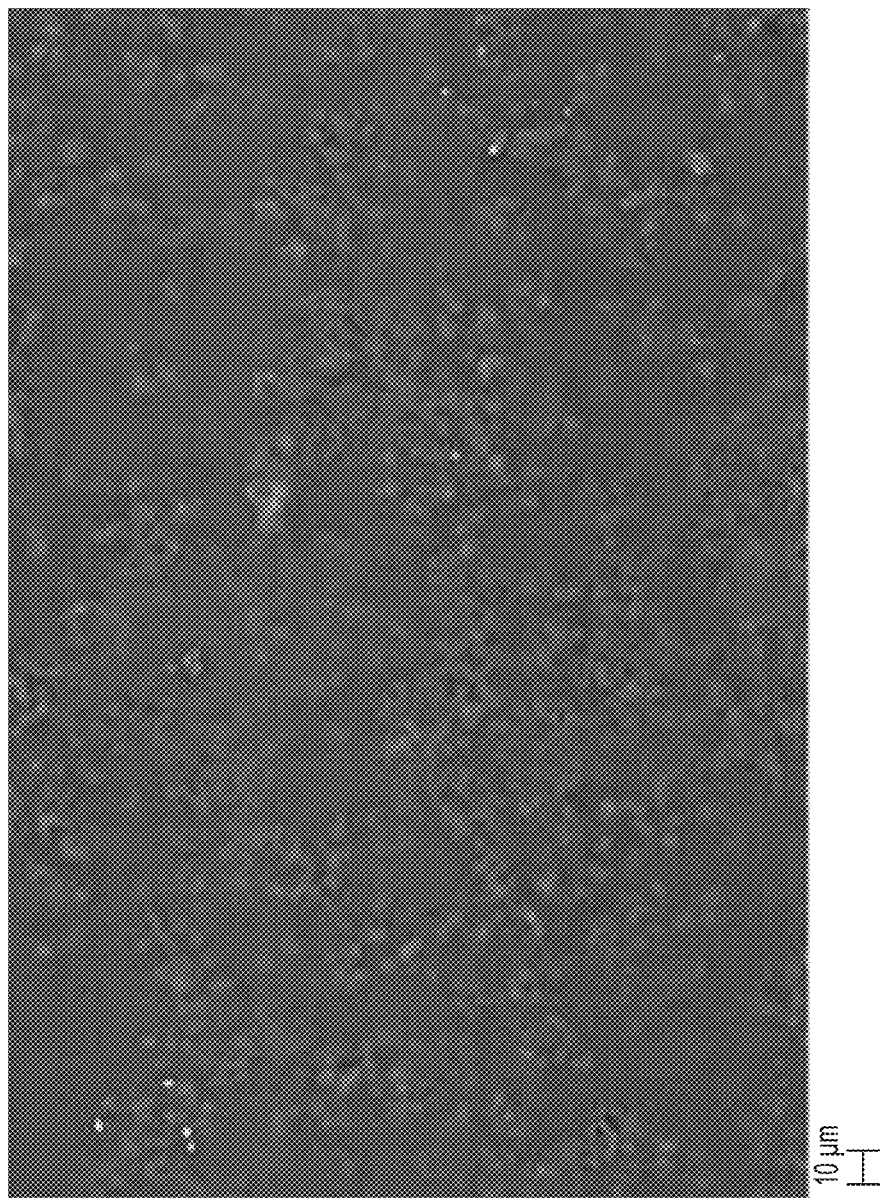
FIG. 6 is a scanning electron microscopy photograph of the surface of an implant containing a first covalently bound chitosan layer, a second layer of chitosan containing vancomycin dispersed therein and a third layer coating of PHEMA.

The outer PHEMA layer was observed to penetrate the second chitosan-vancomycin layer to produce a relatively crack-free coating. Compare, FIG. 5 which is the chitosan-vancomycin layer without the PHEMA layer (including an insert SEM shot at lower magnification) and FIG. 6 which represents the PHEM over the chitosan-vancomycin layer. As may be observed, the PHEMA coating provides relatively smooth surface morphology and as noted herein, increases the mechanical strength of the outer layer, which may be understood as an increase in Shore hardness and/or tensile strength and/or crack initiation) while providing for desirable drug-delivery kinetics. Attention is also directed to FIG. 7, which shows the critical load in milli-newtons (mn) to initiate a crack for the chitosan-vancomycin layer versus that situation where the chitosan-vancomycin layer is covered with an outer layer of PHEMA. The chitosan-vancomycin layer and the chitosan-vancomycin with the PHEMA outer layer were tested on the above referenced CSM NanoScratch Tester according to the following protocol:

| NanoScratch Testing | | |
|---|---|---|
| Sample | Ti Nail/Chitosan-Vancomycin Layer | Ti Nail/Chitosan-Vancomycin Layer & PHEMA Outer Layer |
| Linear Scratch Type: | Progressive | Progressive |
| Initial Load (mN) | 0.3 | 5 |
| Final Load (mN) | 100 | 1000 |
| Loading Rate (mN/min) | 100 | 1000 |
| Scanning Load (mN) | 0.3 | 5.0 |
| Speed (µm/min) | 2006.02 | 2010.05 |
| Length (µm) | 2000 | 2000 |
| Acoustic Emission Sensitivity | 9 | 9 |
| Acquisition Rate | 10 Hz | 10 Hz |

Figure 7:
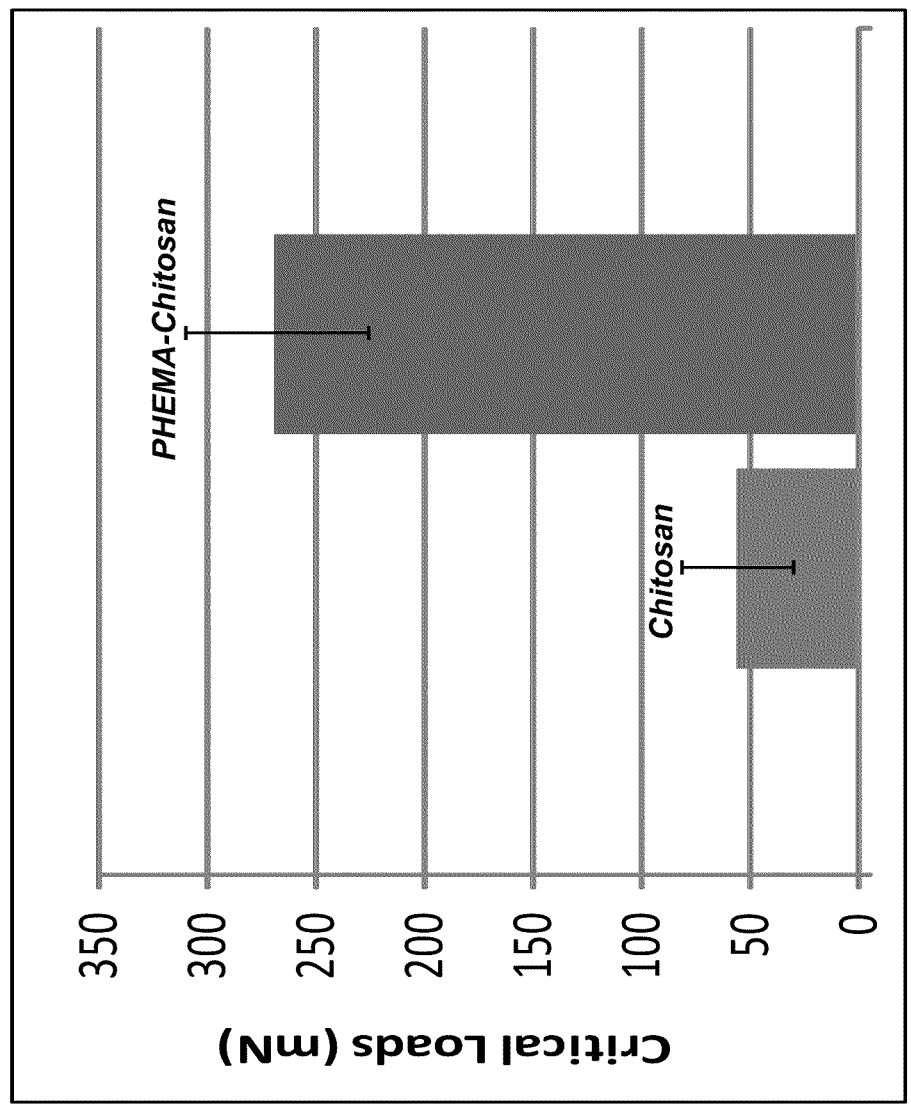
FIG. 7 shows the critical load in millinewtons (mN) to initiate a crack for the chitosan-vancomycin layer on an implant versus an implant containing a chitosan-vancomycin layer and a PHEMA layer.

As can be seen in FIG. 7, the critical load for crack initiation utilizing the PHEMA is increased, to the range of 225 nm to 325 nm, with an average of 275 nm. This represents about a five-fold increase in the average value compared to that situation where the chitosan-vancomycin layer does not contain a PHEMA outer layer (i.e. the chitosan vancomycin layer indicating a critical load to initiation cracking in the range of 25 nm to 85 nm with an average of 55 nm). Consistent with such observation, it may be appreciated that the outer layer herein may be one that provides a relatively greater hardness than any of the inner layers, such as a higher Shore Hardness value.

Example 2

Vancomycin Release

The release of vancomycin from the above Ti-coated rods was evaluated by extraction of the vancomycin into 8 mL phosphate buffer saline (PBS) at various time intervals over 15 days. After each time interval, the solution was decanted for measurement and fresh PBS was added. The released drug was quantified by UV-Vis spectroscopy (Lambda 900 UV-Vis-NIR spectrometer).

Figure 8:
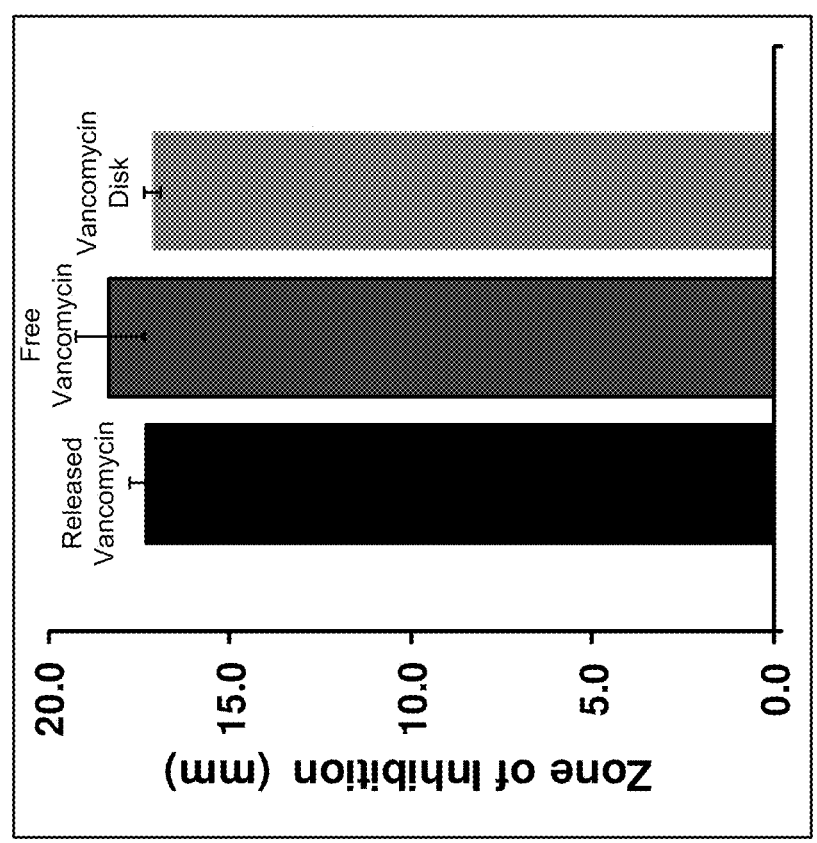
FIG. 8 illustrates zone of inhibition testing for released vancomycin, free vancomycin, and a standard vancomycin disk (loaded with 30 μg of vancomycin).

Bacteria inhibition tests were performed on Agar according to the standard method by using methicillin resistant *Staphylococcus aureus* (MRSA) bacteria (strain: ATCC#33591) in order to determine if the released vancomycin was active and unaffected by the coating and polymerization procedures described herein. The bacteria suspensions were cultured onto separate Mueller-Hinton agar plates at a concentration of $1-2 \times 10^8$ CFU/mL (CFU=colony forming unites) and incubated at 37° C. Released vancomycin, free vancomycin, and a standard vancomycin disk (loaded with 30 µg of vancomycin) were compared. See FIG. 8. After 24 hrs, the zone of inhibition was measured. To measure the sensitivity or the minimum inhibition concentration (MIC), different concentrations of vancomycin were loaded onto cellulose discs (40, 20, 10, 5, 2.5, and 1.25 µg per disc, N=3) and the zone of inhibition was measured.

Figure 9:
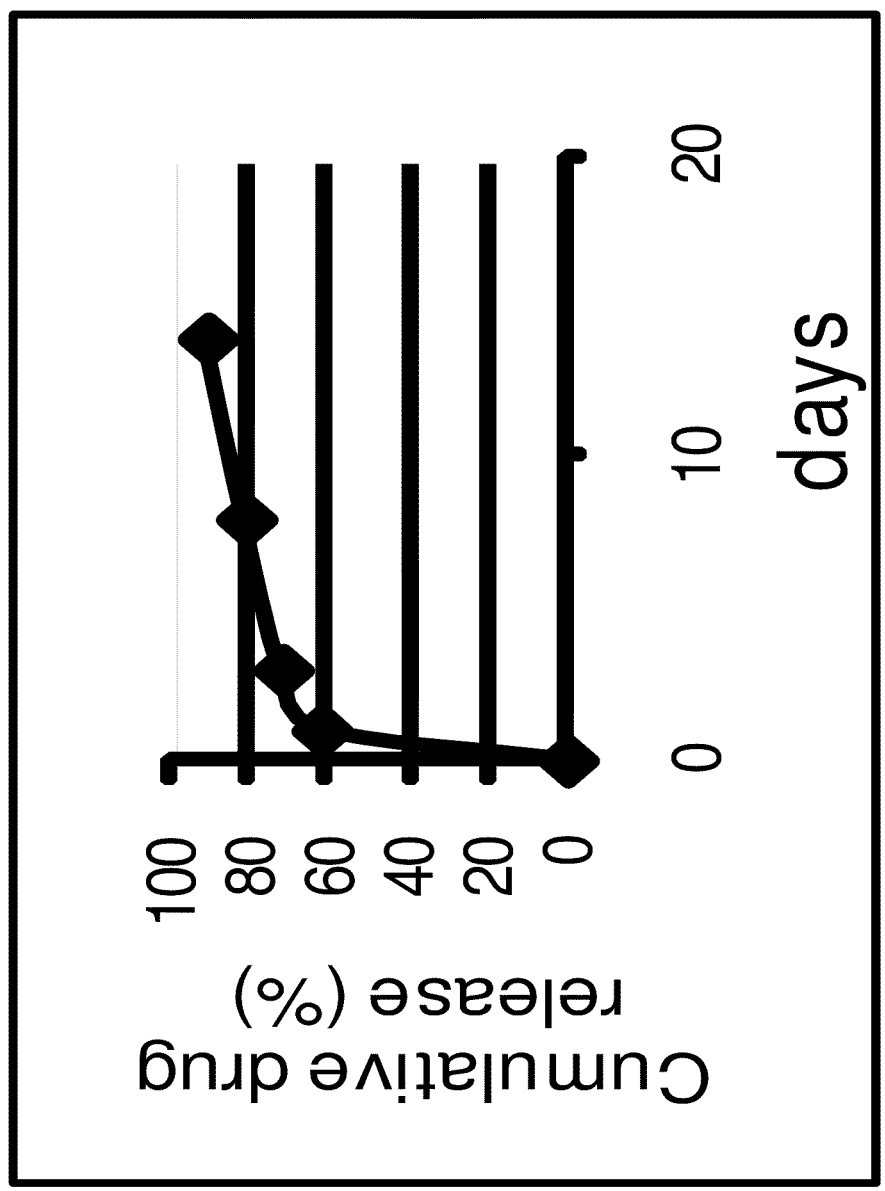
FIG. 9 illustrates cumulative drug release profiles for a Ti IM nail containing covalently bound chitosan, a vancomycin-chitosan layer and a PHEMA layer.
Figure 10:
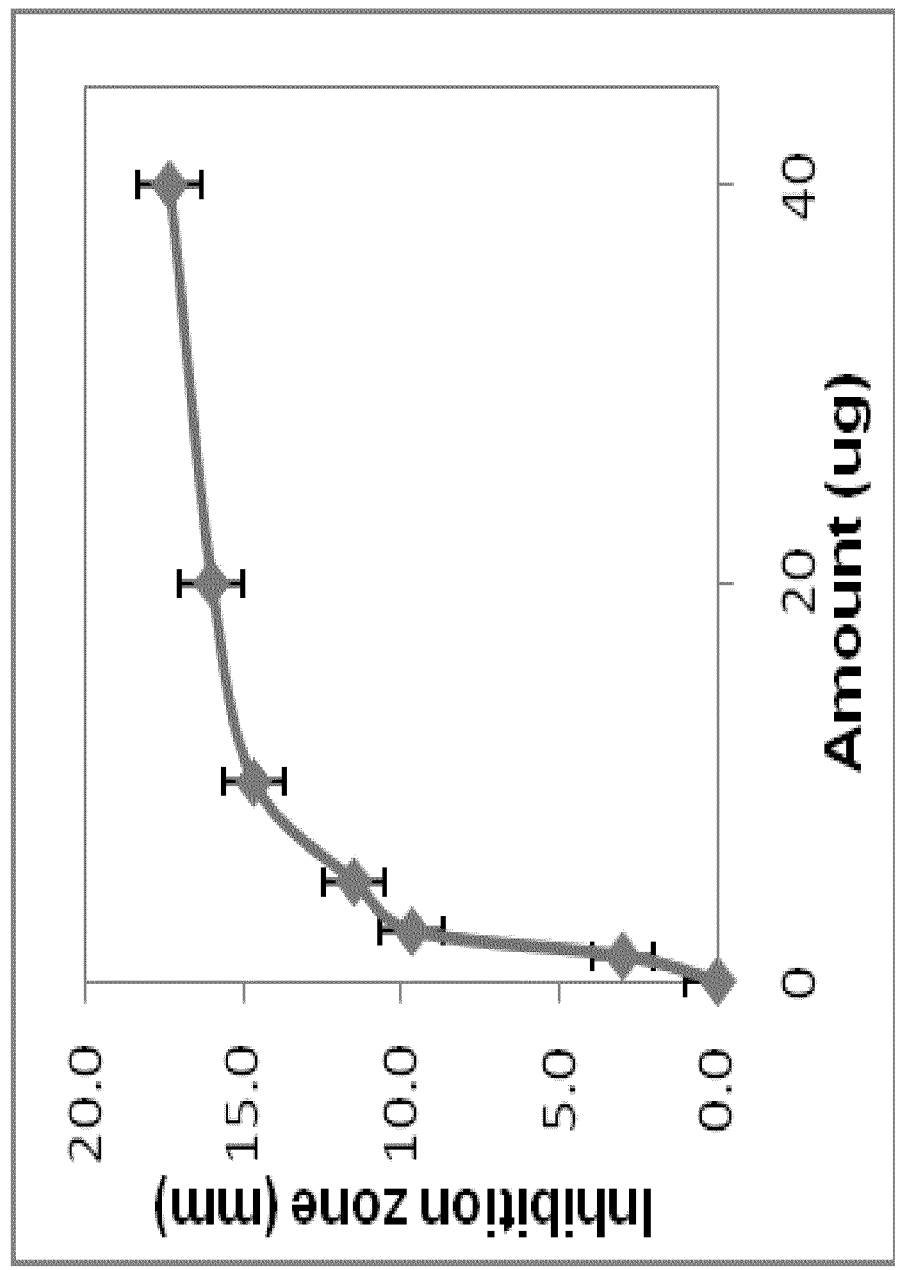
FIG. 10 illustrates bacteria inhibition tests for a Ti IM nail containing covalently bound chitosan, a vancomycin-chitosan layer and a PHEMA layer.

Drug release profiles confirmed that there is an initial burst release of vancomycin from the composite coating (i.e. a Ti IM nail containing covalently bound chitosan, a vancomycin-chitosan layer and a PHEMA layer) followed by a sustained release for up to 2 weeks. See FIG. 9. The bacteria inhibition test indicates that the released drug has the same activity as the free drug and standard drug See FIG. 10. As shown in FIG. 10, the MIC of vancomycin against *S. Aureus* is within the range of 0.5-1 µg similar to that reported in the literature.

Example 3

Lovastatin Coatings

Figure 11:
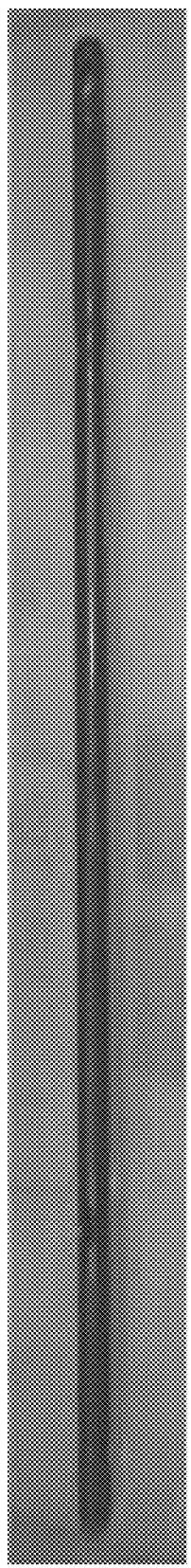
FIG. 11 is a photograph of a PHEMA-PEG-chitosan coating on a Ti nail.

An IM nail was prepared in accordance with the present disclosure, containing a Ti surface covalently bonded to chitosan, followed by a PEG-lovastatin layer and an outer layer of PHEMA. More specifically, a layer of chitosoan was covalently bonded to the Ti surface utilizing a coupling agent. A solution containing 200 mg of lovastatin and 100 mg of PEG (Mw=3500) was prepared by dissolving the lovastatin and PEG in 1.5 mL of $CHCl_3$. 169 ul of this solution was deposited on the chitosan coated Ti surface. A relatively smooth coating formed on the Ti surface after solvent evaporation. Then 20 ul of HEMA monomer solution was deposited on the above Ti and a PHEMA coating was formed after 9 min. photo-polymerization under UV light. See FIG. 11.

It is noted that with respect to the IM implants that are disclosed herein, which may be inserted into reamed bone cavities, such may not be configured to release a selected drug (e.g. an antibiotic, an anabolic, etc.) in a regulated timed fashion to enhance bone growth useful for healing of relatively long bone defects with relatively large gaps. It is therefore contemplated that the IM implants will initiate the release of an anabolic (growth promoting) statin in a controlled manner to promote differentiation of stem cells in a contained autologus (from the patient's body) implant surrounding the IM nail. In addition, it is contemplated herein that the IM nails may include a bioresorbable cowling of selected porosity to further control the transport of material in and out of the implant and to mediate soft tissue ingrowth into the implant.

What is claimed is:

1. A method for coating the surface of an implant comprising:
   (a) exposing the implant surface to a silane coupling agent, wherein said implant surface is a metallic material;
   (b) treating said implant surface with an aliphatic dialdehyde and bonding said dialdehyde to said silane coupling agent via imine functionality;
   (c) coating the implant surface with a first layer of polymeric material that is covalently bound to the implant surface, wherein said first polymeric material includes one or more of the following: chitosan, chitin or gelatin;
   (d) coating the first layer of polymeric material with a second layer of polymeric material wherein the second layer of polymeric material includes a drug for delivery and wherein said second layer of polymeric material is physically adhered to the first layer;
   (e) coating the second layer with a third outer layer; and
   (f) polymerizing said third outer layer,
   wherein said third outer layer is joined to the second layer in the form of an interpenetrating polymer network wherein said second and third layers become interlaced and said third outer layer penetrates into said second layer 1.0 μm to 5.0 μm prior to polymerization,
   wherein said third layer has higher mechanical strength than said first and second layers and is capable of hydration and said implant provides an initial cumulative drug release within 24 hours of administration of 0-95% and a sustained release of any remaining portion within a 14 day period.

2. The method of claim 1 wherein said first layer has a thickness of 10 nanometers to 100 nanometers.

3. The method of claim 1 wherein said second layer has a thickness of 100 nm to 500 μm.

4. The method of claim 1 wherein the outer layer of the implant comprises a polymer of the following formula:

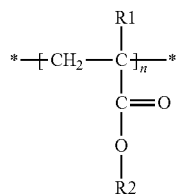

wherein R1 is selected from a hydrogen, alkyl group and/or an aromatic ring;
R2 is selected from the group consisting of: (1) an alkyl group wherein at least one hydrogen on the alkyl group may be substituted with a hydrophilic type functional group; (2) ether and/or polyether type functionality.

5. The method of claim 4 wherein the polymer is poly-2-hydroxyethylmethacrylate and the value of n is greater than 34 to a value of 100.

6. The method of claim 1 wherein the surface of the implant includes a coupling agent to covalently bond said first layer to the surface of said implant.

7. The method of claim 1 wherein said outer layer is capable of absorbing 1.0% by weight to 50.0% by weight water.

8. The method of claim 1 wherein said metallic material is selected from the group consisting of Ti, Al, V, Cr, Fe, Co, Mo, Ni, Mn, Mg, Zr, and combinations thereof and/or stainless steels.

9. The method of claim 1 wherein said second layer comprises one or more of chitosan, collagen, gelatin, chitin, cellulose material, and/or PEG.

10. The method of claim 1 wherein said drug comprises an antibiotic, a statin, an anti-tumor agent, an anti-inflammatory agent; a therapeutic agent, an enzyme or cofactor; a cytokine; an anticoagulant; an immune system factor.

11. The method of claim 1 wherein said second layer and said outer layer have a thickness of 100 nm to 500 μm.

12. A method for coating the surface of an implant comprising:
   (a) exposing the implant surface to a silane coupling agent, wherein said implant surface is a metallic material;
   (b) treating said implant surface with an aliphatic dialdehyde and bonding said dialdehyde to said silane coupling agent via imine functionality;
   (c) coating the implant surface with a first layer of polymeric material that is covalently bound to the implant surface by said coupling agent wherein said first polymer material includes surface functionality comprising amine, hydroxyl and/or carboxylic acid groups and includes one or more of the following: chitosan, chitin or gelatin;
   (d) coating the first layer of polymeric material with a second layer of polymeric material wherein the second layer of polymeric material includes surface functionality comprising amine, hydroxyl and/or carboxylic acid and said second layer includes a drug for delivery and wherein said second layer of polymeric material is physically adhered to the first layer;
   (e) coating the second layer with a third outer layer; and
   (f) polymerizing said third outer layer, wherein said third outer layer is joined to the second layer in the form of an interpenetrating polymer network wherein said second and third layers become interlaced, said third outer layer penetrates into said second layer 1.0 μm to 5.0 μm prior to polymerization and said third outer layer comprises:

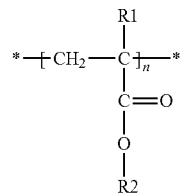

wherein R1 is selected from a hydrogen, alkyl group and/or an aromatic ring;
R2 is selected from the group consisting of: (1) an alkyl group wherein at least one hydrogen on the alkyl group may be substituted with a hydrophilic type functional group; (2) ether and/or polyether type functionality.

13. The method of claim 12 wherein said first layer has a thickness of 10 nanometers to 100 nanometers.

14. The method of claim 12 wherein said second layer has a thickness of 100 nm to 500 μm.

15. The method of claim 12 wherein the polymer is poly-2-hydroxyethylmethacrylate and the value of n is greater than 34 to a value of 100.

16. The method of claim 12 wherein said outer layer is capable of absorbing 1% by weight to 50% by weight water.

17. The method of claim 12 wherein said metallic material is selected from the group consisting of Ti, Al, V, Cr, Fe, Co, Mo, Ni, Mn, Mg, Zr, and combinations thereof and/or stainless steels.

18. The method of claim 12 wherein said second layer comprises one or more of chitosan, collagen, gelatin, chitin, cellulose material, and/or PEG.

19. The method of claim 12 wherein said drug comprises an antibiotic, a statin, an anti-tumor agent, an anti-inflammatory agent; a therapeutic agent, an enzyme or cofactor; a cytokine; an anticoagulant; an immune system factor.

20. The method of claim 12 wherein said second layer and said outer layer have a thickness of 100 nm to 500 μm.

21. An implant comprising:
(a) an implant substrate including an outer surface wherein the implant is a metallic material selected from the group consisting of Ti, Al, V, Cr, Fe, Co, Mo, Ni, Mn, Mg, Zr, and combinations thereof and/or stainless steels wherein said metallic material has a surface having a silane coupling agent that is bonded to an aliphatic dialdehyde via imine functionality;
(b) a first layer of polymeric material that is covalently bound to the implant surface, wherein said first layer includes one or more of the following: chitosan, chitin or gelatin;
(c) a second layer of polymeric material wherein the second layer of polymeric material includes a drug for delivery and wherein said second layer of polymeric material is physically adhered to the first layer; and/or
(d) a third outer layer wherein said third outer layer is joined to the second layer in the form of an interpenetrating polymer network, wherein said second and third layers become interlaced and said third outer layer penetrates into said second layer at a depth of 1.0 μm to 5.0 μm prior to polymerization;

wherein said third layer has higher mechanical strength than said first and second layers and is capable of hydration and said implant provides an initial cumulative drug release within 24 hours of implantation of 0-95% and a sustained release of any remaining portion within a 14 day period.

22. An implant comprising:
(a) an implant substrate including an outer surface wherein the implant is a metallic material selected from the group consisting of Ti, Al, V, Cr, Fe, Co, Mo, Ni, Mn, Mg, Zr, and combinations thereof and/or stainless steels wherein said metallic material has a surface having a silane coupling agent that is bonded to an aliphatic dialdehyde via imine functionality;
(b) a first layer of polymeric material including a drug for delivery wherein said polymer material is covalently bound to the implant surface by said coupling agent wherein said first polymer material includes surface functionality comprising amine, hydroxyl and/or carboxylic acid groups;
(b) a second layer of polymeric material which includes surface functionality comprising amine, hydroxyl and/or carboxylic acid and said second layer includes a drug for delivery and wherein said second layer is physically adhered to the first layer;
(c) a third outer layer wherein said third outer layer is joined to the second layer in the form of an interpenetrating polymer network and wherein said second and third layers are interlaced and said third outer layer penetrates into said second layer 1.0 μm to 5.0 μm and said third outer layer comprises:

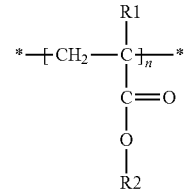

wherein R1 is selected from a hydrogen, alkyl group and/or an aromatic ring;
R2 is selected from: (1) an alkyl group wherein at least one hydrogen on the alkyl group may be substituted with a hydrophilic type functional group; (2) ether and/or polyether type functionality.

* * * * *